United States Patent
Kwasnick et al.

(10) Patent No.: US 6,422,750 B1
(45) Date of Patent: Jul. 23, 2002

(54) DIGITAL X-RAY IMAGER ALIGNMENT METHOD

(75) Inventors: Robert Forrest Kwasnick, Palo Alto; Paul Richard Granfors, Sunnyvale, both of CA (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/745,678

(22) Filed: Dec. 22, 2000

(51) Int. Cl.$^7$ ............................... G03C 5/16
(52) U.S. Cl. .............................. 378/205; 378/154
(58) Field of Search ......................... 378/154, 205

(56) References Cited

U.S. PATENT DOCUMENTS

| | | | |
|---|---|---|---|
| 5,241,578 A | * 8/1993 | MacMahon | 378/154 |
| 5,303,282 A | 4/1994 | Kwasnick et al. | |
| 5,557,650 A | * 9/1996 | Guida et al. | 378/154 |
| 5,684,851 A | * 11/1997 | Kurbatov et al. | 378/87 |
| 5,715,292 A | * 2/1998 | Sayag et al. | 378/98.8 |
| 5,784,431 A | * 7/1998 | Kalend et al. | 378/65 |
| 6,081,577 A | * 6/2000 | Webber | 378/23 |
| 6,106,152 A | * 8/2000 | Thunberg | 378/205 |
| 6,139,520 A | * 10/2000 | McCrory et al. | 604/60 |

FOREIGN PATENT DOCUMENTS

JP        402191936 A  * 7/1990 ................ 378/154

OTHER PUBLICATIONS

Carlin et al. (1996) "The Effect of X–Ray Beam Alignment on the Performance of AntiScatter Grids", *Med. Phys.* 23(8):1347–1350.

MacMahon et al. (1992) "Laser Alignment System for High–Quality Portable Radiography", *Radiographics* 12:111–120.

MacMahon et al. (1996) "Portable Chest Radiography Techniques and Teleradiology" *Radiologic Clinics of North America* 34(1):1–20.

* cited by examiner

Primary Examiner—David P. Porta
Assistant Examiner—Elizabeth Gemmell
(74) Attorney, Agent, or Firm—Collard & Roe, PC

(57) ABSTRACT

In a digital x-ray imager alignment method, a low exposure x-ray image of an object is taken. The dose is sufficient to create an image of an object and alignment bars on an antiscatter grid. The relative position of the alignment bars on the image is measured. The relative angle of the detector to the x-ray source is adjusted. This adjustment brings the grid into alignment with the x-ray source. A diagnostic x-ray exposure image of the object is then taken.

20 Claims, 2 Drawing Sheets

DIGITAL X-RAY IMAGER ALIGNMENT METHOD

BACKGROUND OF THE INVENTION

1. Field of the Invention

The present invention relates to x-ray imaging. More particularly, an alignment method is provided for a digital x-ray imager suitable for use in medical diagnostic applications.

2. The Prior Art

In x-ray imaging, it is generally desirable to minimize x-ray exposure to the amount required to achieve acceptable image quality. For medical diagnostic imaging the goal is to keep the x-ray exposure of the patient to the minimum needed. For other applications such as industrial inspection or veterinary studies, x-ray source (tube and generator) life is limited. Here again it is desirable to use no more exposure than needed.

The x-ray imaging set up usually comprises at least an x-ray source, a patient (or other object under study), and a detector. The origin of x-rays within the x-ray source is generally on the order of 1 mm. The distance is small relative to the distance between the source and the detector (on the order of 1 m).

It is desirable to have an x-ray quality that is as good as possible to enhance the utility of the x-ray image. Often antiscatter grids are used to improve x-ray image quality. Typically, the grid and detector are attached to form a detector/grid assembly. The antiscatter grid is generally formed from alternating strips of x-ray opaque material and x-ray transmissive materials. Lead may be used as the x-ray opaque material and plastics, aluminum or fiber may be used as the x-ray transmissive material. Two dimensional arrangements of x-ray opaque and transmissive materials (or air) are possible also. In either arrangement, the grid substantially transmits unscattered (primary) x-rays and substantially absorbs x-rays scattered by the patient or object under study, thereby preventing the scattered x-rays from degrading image quality. This function is accomplished by aligning the strips parallel to the primary x-rays. In some applications, for example, portable x-ray examinations, a patient is examined while prone in a hospital bed. In these applications, the detector/grid is not mechanically aligned perpendicular to the source, which can degrade the grid's functionality.

Dr. Heber MacMahon, at the University of Chicago, uses a technique involving alignment bars. In his technique, small alignment bars are attached to the front and back sides of the antiscatter grid. The alignment bars may be about 1 mm by 10 mm in area and 0.1 to 1 mm in thickness. The bars are substantially aligned with each other on opposite sides of the same septa of the grid. In other words, they are disposed on each side of the grid and overlap at least one of the spaces formed by the x-ray transmissive grid parts. The detector typically comprises either film or photostimulable phosphor. If the detector is not aligned correctly, the two alignment bars appear in different positions in the image. Misalignment correlates with lower quality images.

However, this alignment information is obtained only after the detector is removed and the latent image is developed. Hence, it cannot be used to improve the image in situ. At best, the alignment information can be used only to indicate after the fact whether the image quality is good. Additional images, resulting in more x-ray exposure, may need to be taken if the image quality is poor.

Hence, a method using alignment information to improve the first diagnostic image is still needed. Also needed is a method that reduces the amount of x-ray exposure required to achieve acceptable image quality.

BRIEF SUMMARY OF THE INVENTION

A digital x-ray imager method is provided for use, for example, in medical diagnostic applications. The method is particularly useful in planar detectors used in portable imaging applications. In such applications, the detector surface is not mechanically constrained to be perpendicular to the central x-ray source beam. The method requires only an insignificant increase in x-ray exposure. The method also achieves a substantially optimal quality diagnostic image in digital x-ray imaging systems. A digital x-ray imaging system is provided including an x-ray source and a detector. An antiscatter grid is attached to the detector and disposed between the detector and the object under study, for example, a patient. The grid has at least one pair of substantially x-ray opaque alignment bars. Preferably, the antiscatter grid has alternating strips of x-ray opaque material (lead) and x-ray transmissive material (for example, plastic, aluminum, fiber or air). The grid has front and back surfaces on which the alignment bars are disposed, one of each pair on each surface.

A low exposure non-diagnostic x-ray image is taken with a dose sufficient to create an image of the alignment bars on the object. For example, the low x-ray dose may be about 0.001 to 0.01 of that used for the diagnostic x-ray image. The relative position of the alignment bars on the image is measured, for example, manually or by a computer algorithm. The relative angle of the detector to the x-ray source is adjusted to align the grid with the x-ray source. The adjustment required is the arc tangent of the distance between the alignment bars in the image divided by the antiscatter grid thickness. A diagnostic x-ray exposure image is then taken of the object. Alternatively, a second low exposure image may be taken to confirm alignment prior to taking the diagnostic x-ray exposure image.

BRIEF DESCRIPTION OF THE DRAWINGS

Other objects and features of the present invention will become apparent from the following detailed description considered in connection with the accompanying drawings. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

Figure 1:
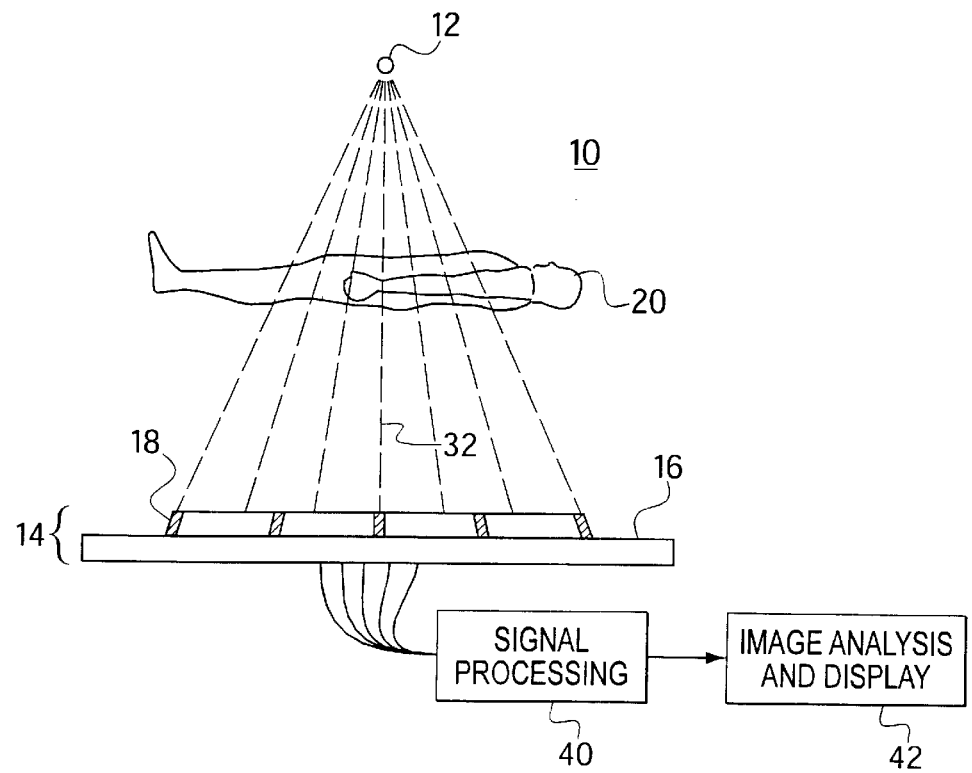
FIG. 1 is a schematic diagram of a projection x-ray imaging device incorporating an antiscatter grid with alignment bars used in the present invention.

Referring to FIG. 1, a digital radiation imager system 10, such as a medical x-ray projection imaging system, is shown. FIG. 1 shows a schematic diagram, not drawn to scale, of a typical system. The projection x-ray imaging system 10 comprises a radiation point source 12, typically an x-ray source. The imaging system 10 also includes a radiation detector/antiscatter grid assembly 14 including a radiation detector 16 and an antiscatter grid 18. The origin of x-rays within x-ray source 12 is generally small relative to the distance between source 12 and detector 16. The distance between source 12 and detector 16 is on the order of 1 m. The origin of x-rays is on the order of 1 mm in spatial extent. Detector 16 includes a radiation detector panel (not shown) that converts incident radiation into electrical signals. The detector elements of the detector panel are typically arranged in a two-dimensional array. The elements are coupled to a signal processing circuit 40 and from there to an image analysis and display circuit 42. The surface of the detector/antiscatter grid assembly 14 may not be constrained by mechanical means to be perpendicular to the central ray of x-ray source 12.

Figure 2:
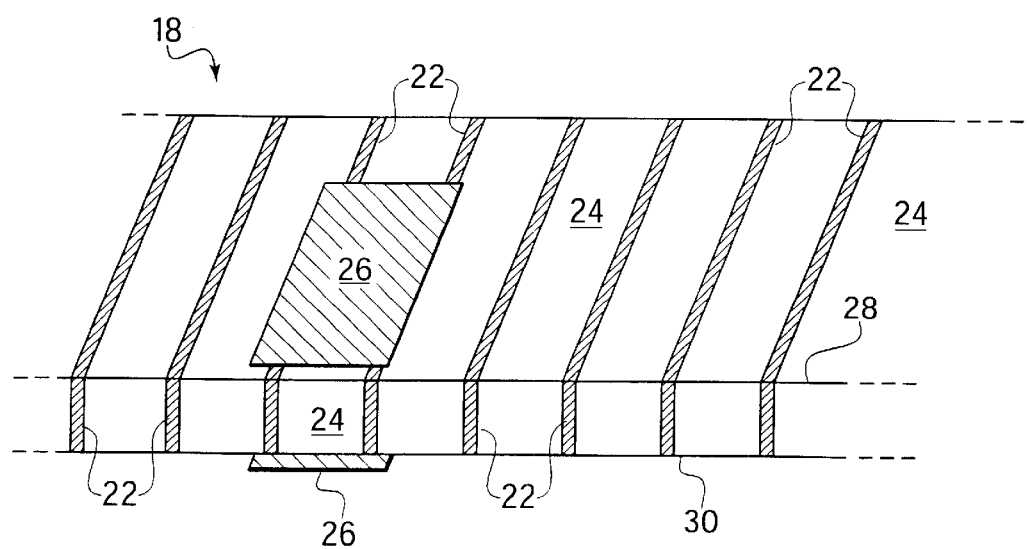
FIG. 2 is a perspective view of the antiscatter grid with alignment bars of FIG. 1.

Antiscatter grid 18 is attached to detector 16 and disposed between detector 16 and an object, for example, a patient 20 under study. FIG. 2 is a perspective view of a representative portion of antiscatter grid 18. As shown in FIG. 2, antiscatter grid 18 comprises alternating strips of x-ray opaque material 22 and x-ray transmissive material 24. X-ray opaque material 22 may be lead. X-ray transmissive material 24 may be plastic, aluminum, fiber or air. A typical grid may have dimensions of about 41 cm by 41 cm by 2 mm thick with about 78 lead strips per cm. Each lead strip is about 1.3 mm tall by 28 $\mu$m wide and the spacing between the lead strips for the x-ray transmissive portion of the grid is about 100 $\mu$m.

Antiscatter grid 18 includes at least one pair of substantially x-ray opaque alignment bars 26, preferably disposed on front surface 28 and back surface 30 of grid 18. They are positioned at opposite sides of the same septa, or, more generally, aligned along the line defined by an x-ray beam 32. Preferably, the alignment bars are positioned towards the edge of the detector where they do not interfere with the central region of the image. Alignment bars 26 are preferably lead but may be another substantially x-ray opaque material such as tungsten. Alignment bars 26 are generally 1 mm by 10 mm in area and 0.1 to 1 mm in thickness. Bars 26 are disposed parallel to and preferably substantially centered on opposite sides of the same septa 24 of grid 18. Bars 26 generally will be much wider than grid septa 24. Preferably one pair of bars 26 are provided on the front 28 and back 30 surfaces of grid 18, but additional pairs of alignment bars 26 may be used. In particular, it is useful to have two pairs of alignment bars on opposite edges of the detector in order to more accurately determine the angular alignment when the source is not exactly at the focal spot of the grid. Each pair of alignment bars 26 is positioned precisely so that the image of bars 26 is superimposed when the central x-ray beam is aligned with grid 18.

In performing an alignment, a low exposure x-ray image of the object 20 is taken. The dose could be as low as a few microRoentgen exposure to the detector. This dose is sufficient to create an image of alignment bars 26 on the object. Generally, lower dose is desirable when imaging human subjects. Typically, the dose is about 1% and may be as low as 0.1% of that used for the diagnostic image. This dose is sufficient with digital x-ray detectors to observe alignment bars 26. The low exposure x-ray image is preferably taken after preliminary alignment of detector/grid assembly 14 to x-ray source 12. The low exposure x-ray image is observed and the relative position of alignment bars 26 is measured on the image. This measurement can be done manually or automatically. For example, a computer algorithm could be readily designed by one skilled in the art to take the required measurement. The positions of source 12 and/or detector/grid assembly 14 are then adjusted to bring grid 18 into alignment with x-ray source 12. A second low exposure image may than be taken to confirm alignment. If alignment is not confirmed, additional adjustment and confirming images may be performed. Thereafter, the high exposure diagnostic image of object 20 is taken. The high exposure is typically several hundred microRoentgen exposure to the detector.

Figure 3:
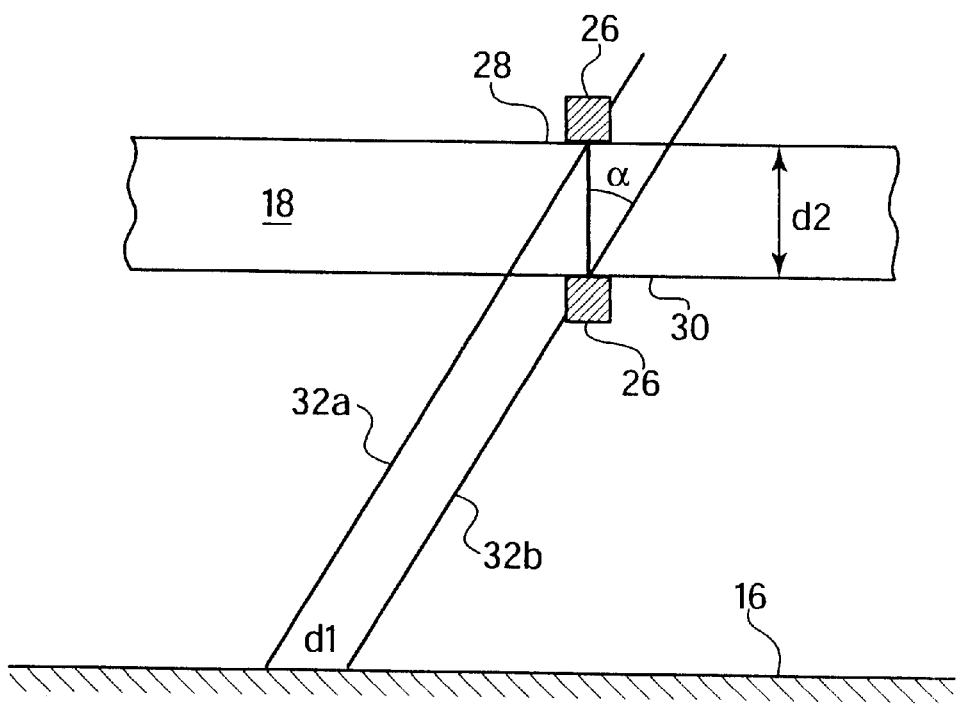
FIG. 3 is a schematic diagram of the path of exemplary x-rays through the antiscatter grid to the detector with the alignment bars of FIG. 1 showing misalignment of x-ray source and antiscatter grid.

FIG. 3 illustrates a preferred method of determining angular misalignment, 10 and thus the adjustment required by either source 12 or detector/grid assembly 14. (By way of illustration, the bars are shown as being in the center of the grid so that alignment bars 26 are at the same relative position on grid 18.) FIG. 3 illustrates an exemplar pair of x-ray beams 32a, 32b. One beam of the pair passes through the top alignment bar, and the other beam passes through the same part of the bottom indicator bar. One alignment bar 26 is disposed on front surface 28 and another alignment bar 26 is disposed on back surface 30 of antiscatter grid 18. Hence the distance d2 between the bars is the thickness of antiscatter grid 18. Beam 32a creates an image of bar 26 on front surface 28, and beam 32b creates an image for bar 26 on back surface 30. As shown in FIG. 3, the low dose radiation creates an image of bars 26 that shows misalignment of the x-ray source and the grid, i.e. the x-rays are not perpendicular to grid 18 but rather are misaligned by an angle $\alpha$. The misalignment results in an image of the alignment bars with a separation of distance di between them in the image. The angular misalignment, and thus the adjustment required of the relative angle of detector 16 to source 12 may be easily determined. The adjustment is the arctangent of the distance d1 between the bars in the image divided by the antiscatter grid thickness d2. In proper alignment, the image of the alignment bars overlap each other to form a single line in the image (d1=0).

Thus, as described above, a series of low-level exposures is used for the alignment. This alignment method is useful to align a digital x-ray detector to the x-ray source in various systems. The method is particularly useful in portable imaging applications. In many such applications, the detector surface is not constrained by mechanical means relative to the x-ray source. Thus, the detector surface is not mechanically constrained to be perpendicular to the central ray of the x-ray source, but rather is aligned during the imaging procedure. An x-ray antiscatter grid is provided in proximity to and attached to the detector. The grid is disposed between the detector and the patient or object under study. The grid has small, substantially x-ray opaque, alignment bars on both its front and back surfaces. A low x-ray dose image is taken and the positions on the image of the alignment bars are measured. Then the x-ray source, and/or the detector/grid assembly, is moved into alignment before the diagnostic high exposure image is taken.

While preferred embodiments of the present invention have been shown and described, it is to be understood that many changes and modifications may be made thereunto without departing from the spirit and scope of the invention as defined in the appended claims.

What is claimed is:

1. A method for aligning a digital x-ray imaging system comprising an x-ray source, an antiscatter grid, and a detector, the grid being attached to the detector and disposed between the detector, and an object under study, the grid having a front side and a back side and at least one pair of substantially x-ray opaque alignment bars, one bar of said pair attached to the front side and the other bar of said pair attached to the back side, the method comprising the steps of:

(a) taking a low exposure non-diagnostic x-ray image of the object with a dose sufficient to create an image of the alignment bars on the object;

(b) measuring the relative position on the image of the alignment bars;

(c) adjusting the relative angle of the detector to the x-ray source to bring the grid into alignment with the x-ray source; and (d) taking a diagnostic x-ray exposure image of the object.

2. The method according to claim 1 wherein the low exposure x-ray image is taken with an x-ray dose about 0.1% to it of the x-ray dose used for the diagnostic x-ray exposure image.

3. The method according to claim 1 wherein the antiscatter grid is formed from alternating strips of x-ray opaque material and x-ray transmissive material.

4. The method according to claim 3 wherein the x-ray opaque material is lead and the x-ray transmissive material is selected from the group consisting of plastic, aluminum, fiber and air.

5. The method according to claim 1 wherein the measuring step is performed by computer algorithm.

6. The method according to claim 1 wherein the measuring step is performed manually.

7. The method according to claim 1 further comprising taking a second low exposure x-ray image of the object prior to the step of taking a diagnostic x-ray exposure image in order to confirm alignment.

8. The method according to claim 1 wherein the adjustment of the relative angle of the detector to the x-ray source is the arctangent of the distance d1 between the alignment bars in the image divided by the thickness of the antiscatter grid.

9. The method according to claim 1 wherein the alignment bars are made from lead.

10. The method according to claim 1 wherein the alignment bars are made from tungsten.

11. A method for aligning a digital x-ray imager comprising the steps of:

(a) providing a portable digital x-ray imaging system comprising an x-ray source, an antiscatter grid, and a planar detector, the grid being attached to the detector and disposed between the detector and an object under study, the grid having front and back surfaces separated by a distance d2 and at least one substantially x-ray opaque alignment bar on each of said surfaces;

(b) taking a first low level x-ray exposure to create an image of the object and of the alignment bars on the object;

(c) measuring the distance d1 between the alignment bars on the image;

(d) adjusting the relative angle of the detector to the x-ray source by the arctangent of the distance d1 between the bar divided by the distance d2;

(e) taking a second low level x-ray exposure to confirm alignment of the grid with the x-ray source; and (f) taking a diagnostic x-ray exposure image of the object.

12. The method according to claim 11 wherein the low level x-ray exposures are taken with an x-ray dose about 0.1% to 1% of the x-ray dose used for the diagnostic x-ray exposure image.

13. The method according to claim 11 wherein the antiscatter grid is formed from alternating strips of x-ray opaque material and x-ray transmissive material.

14. The method according to claim 11 wherein the x-ray opaque material is lead and the x-ray transmissive material is selected from the group consisting of plastic, aluminum, fiber and air.

15. The method according to claim 11 wherein the measuring step is performed by computer algorithm.

16. The method according to claim 11 wherein the measuring step is performed manually.

17. The method according to claim 11 wherein the alignment bars are made from lead.

18. The method according to claim 11 wherein the alignment bars are made from tungsten.

19. The method according to claim 1 further comprising repeating steps (a) through (c) until satisfactory alignment is achieved prior to the step of taking a diagnostic x-ray exposure image.

20. The method according to claim 11 further comprising repeating steps (b) through (d) until satisfactory alignment is achieved prior to the step of taking a diagnostic x-ray exposure image.

* * * * *

UNITED STATES PATENT AND TRADEMARK OFFICE
CERTIFICATE OF CORRECTION

PATENT NO.   : 6,422,750 B1
DATED        : July 23, 2002
INVENTOR(S)  : Robert F. Kwasnick et al.

It is certified that error appears in the above-identified patent and that said Letters Patent is hereby corrected as shown below:

<u>Column 5,</u>
Line 3, please change "it" to -- 1% --.

Signed and Sealed this

Twenty-sixth Day of November, 2002

Attest:

Attesting Officer

JAMES E. ROGAN
*Director of the United States Patent and Trademark Office*